(12) United States Patent
Park et al.

(10) Patent No.: US 11,058,450 B2
(45) Date of Patent: Jul. 13, 2021

(54) PUNCHING NEEDLE AND HANDPIECE USED FOR HAIR EXTRACTION

(71) Applicants: Jae Hyun Park, Seoul (KR); Choon Bae Park, Jeollabuk-do (KR)

(72) Inventors: Jae Hyun Park, Seoul (KR); Choon Bae Park, Jeollabuk-do (KR)

(*) Notice: Subject to any disclaimer, the term of this patent is extended or adjusted under 35 U.S.C. 154(b) by 144 days.

(21) Appl. No.: 16/029,921

(22) Filed: Jul. 9, 2018

(65) Prior Publication Data

US 2018/0325544 A1 Nov. 15, 2018

Related U.S. Application Data

(63) Continuation of application No. PCT/KR2017/005020, filed on May 15, 2017.

(30) Foreign Application Priority Data

May 13, 2016 (KR) .................. 10-2016-0058978
Jul. 22, 2016 (KR) .................. 10-2016-0093747

(51) Int. Cl.
*A61B 17/3205* (2006.01)
*A61B 17/00* (2006.01)
(Continued)

(52) U.S. Cl.
CPC .... *A61B 17/32053* (2013.01); *A61B 10/0233* (2013.01); *A61B 2017/00752* (2013.01);
(Continued)

(58) Field of Classification Search
CPC .... A61B 17/32053; A61B 2017/00752; A61B 2017/320064; A61B 17/32002; A61F 2/10
See application file for complete search history.

(56) References Cited

U.S. PATENT DOCUMENTS

| 8,211,116 B2 | 7/2012 | Oostman, Jr. et al. |
| 2010/0125287 A1* | 5/2010 | Cole ............... A61B 17/32053 606/133 |
| 2016/0249948 A1* | 9/2016 | Umar ............... A61B 17/32053 606/133 |

FOREIGN PATENT DOCUMENTS

| JP | 2010104571 A | 5/2010 |
| KR | 20100023419 A | 3/2010 |

(Continued)

OTHER PUBLICATIONS

International Search Report dated Aug. 21, 2017.
Korean Office Action dated Nov. 7, 2016.
English Translation of Korean Office Action dated Nov. 7, 2016.

*Primary Examiner* — Majid Jamialahmadi
(74) *Attorney, Agent, or Firm* — Dinsmore & Shohl LLP; Yongsok Choi, Esq.

(57) ABSTRACT

A punching needle for a handpiece used to separate a follicle of an extraction target hair from a skin tissue of a patient while the punching needle is rotated is provided. The punching needle includes a slit formed at one side of a front end portion thereof, the slit extends rearward from the front end portion of the punching needle in a longitudinal direction of the punching needle, and the punching needle is mounted in and used in the handpiece to allow a part of the slit or the entire slit to be exposed in front of the handpiece. The punching needle enables an inside of the punching needle to be directly and visually checked through the slit and enables the extraction target hair to be inserted into the punching needle from a side of the punching needle through the slit formed in the punching needle.

10 Claims, 11 Drawing Sheets

(51) Int. Cl.
 *A61B 17/32* (2006.01)
 *A61B 10/02* (2006.01)
(52) U.S. Cl.
 CPC ............... *A61B 2017/00973* (2013.01); *A61B 2017/320028* (2013.01); *A61B 2017/320064* (2013.01)

(56) References Cited

FOREIGN PATENT DOCUMENTS

| KR | 101317310 B1 | 10/2013 |
| KR | 1020140135420 A | 11/2014 |
| KR | 1020140135434 A | 11/2014 |
| KR | 101600758 B1 | 3/2016 |
| WO | 2014082077 A1 | 5/2014 |

\* cited by examiner

PUNCHING NEEDLE AND HANDPIECE USED FOR HAIR EXTRACTION

CROSS-REFERENCE TO RELATED APPLICATIONS

This application is a continuation of PCT/KR2017/005020 filed on May 15, 2017 which claims priority to Korean Patent Application No. 10-2016-0058978 filed on May 13, 2016 and Korean Patent Application No. 10-2016-0093747 filed on Jul. 22, 2016, the entire contents of which are herein incorporated by reference.

TECHNICAL FIELD

The present disclosure relates to a punching needle and handpiece used for extracting a hair from a patient's skin, and more particularly to a punching needle and handpiece which allow a hair to be stably extracted from a patient without cropping the hair in an extraction region and which are configured to reduce a risk of damage to the hair follicle in a process of extracting a hair.

BACKGROUND ART

Hair transplantation is a procedure for transplanting new hairs to a site where hairs have been lost in the case of hair loss on human skin due to diseases or accidents. Hair transplantation may be classified into follicular unit strip surgery (FUSS) and follicular unit extraction (FUE) according to a method of obtaining a hair to be transplanted.

Follicular unit strip surgery refers to a procedure in which a certain scalp area is incised in a donor site, a hair follicle is then extracted from the incised scalp and transplanted to a necessary site, and the incision area of the donor site is stitched with a suture. Such follicular unit strip surgery is currently most used as a method for follicular unit transplantation surgery. However, this surgery has disadvantages in that, because the scalp in the donor site is incised, it causes great pain for a patient and a long and large surgical scar is inevitably generated at the incision area.

Follicular unit extraction is a procedure that has been introduced to overcome the disadvantages of the above-described follicular unit strip surgery. Follicular unit extraction refers to a procedure in which a hair to be transplanted is extracted from patient's skin using a hair follicle separator (i.e., handpiece) without incising a scalp of the patient. Follicular unit extraction has an advantage in that, since this procedure is performed without incising the patient's skin, patient's fear on skin incision may be eliminated and formation of a large surgical scar over a wide area after the procedure may be prevented.

In FIG. 1, a handpiece 10 used for extracting a hair to be transplanted in follicular unit extraction is exemplarily illustrated. By inserting a punching needle 20 mounted in the front of the handpiece 10 into a patient's skin and puncturing the patient's skin, the handpiece 10 performs a function of separating from surrounding tissue a follicle of the extraction target hair. Generally, the handpiece 10 includes an electric motor and a spindle assembly provided therein, and is configured to insert the punching needle 20 into the patient's skin while rotating the punching needle 20 with a rotational force of the electric motor. When the hair follicle is separated from the surrounding tissue using the handpiece 10, the hair may be extracted to the outside by pulling the hair with medical equipment such as forceps.

In order to separate the hair follicle using the handpiece 10 as described above, the extraction target hair is first inserted into the punching needle 20 mounted in the front of the handpiece 10, and the punching needle 20 should then penetrate the patient's skin. At this time, the hair is inserted into the punching needle 20 from an end thereof as shown in FIG. 2. Accordingly, in the follicular unit extraction in which the hair to be transplanted is extracted using the handpiece 10, in order to smoothly perform a punching operation, the hair is extracted in a state in which hairs in an extraction region are cropped to a length of about 1 mm (if the extraction target hair is long, it is difficult to effectively perform the punching operation since it is difficult to insert the hair into the punching needle and/or it takes a long time to insert the hair into the punching needle).

However, when the hairs are closely cropped, office workers or women face great difficulties in their daily lives while the hairs are growing again. Accordingly, they may have a strong repulsion and inconvenience on the hair transplantation procedure. Furthermore, since a length of a hair extracted in a state in which the hairs are closely cropped is too short, it is difficult to carry out the transplantation while accurately matching the extracted hair with surrounding hairs in the recipient site in terms of thickness, curl, etc. Further, it may adversely affect the procedure result even after the transplantation of the hair, since the transplanted hair having too short length may be sunk into the skin and may cause side effects that the transplanted hair may be died or inflammation may be caused at the transplantation site.

In addition, in order to stably extract the hair without damaging the hair follicle, the punching needle 20 should be inserted in a direction of the hair and in a state in which the punching needle 20 is placed so that the hair (preferably, the hair follicle) is centered in the punching needle 20 as shown in FIG. 3A. When the punching needle 20 is inserted in a state biased toward one side as shown in FIG. 3B or inserted in a misaligned direction as shown in FIG. 3C, the hair follicle may be cut or damaged by the punching needle 20 in a process of inserting the punching needle 20 (see the portion "A" in FIG. 3B and the portion "B" in FIG. 3C), and such hair follicle damage causes lowering of the successful transplantation rate and the engraftment rate of the extracted hair follicles.

However, since the punching needle 20 is generally formed of a metal material having high rigidity (for example, stainless steel) so as to stably penetrate the patient's skin, an operator cannot visually check the extraction target hair placed in the punching needle 20, and thus the operator may have big difficulty to set a position and direction of the punching needle 20.

Accordingly, in the conventional follicular unit extraction, the patient is likely to uncomfortable and inconvenience feeling since the procedure should generally be performed in the state that the hairs in the extraction region are closely cropped, and it is difficult to provide high satisfaction on the operation to the patient. Further, the transplantation rate and the engraftment rate of the extracted hair follicles may be reduced since the hair follicle is likely to be cut or damaged in the process of separating the follicle of the extraction target hair.

Technical Problem

The present disclosure is directed to providing a punching needle and handpiece capable of effectively extracting from a patient a hair, which is not cropped and has a relatively long length, and capable of reducing a risk of cutting or damaging a hair follicle in a process of extracting a hair.

Technical Solution

A representative configuration of the present disclosure for achieving the above-described objects is as follows.

According to one embodiment of the present disclosure, there is provided a punching needle for a handpiece used to separate a follicle of an extraction target hair from a skin tissue of a patient while the punching needle is rotated. The punching needle according to one embodiment of the present disclosure includes a slit formed at one side of a front end portion thereof, the slit extends rearward from the front end portion of the punching needle in a longitudinal direction of the punching needle, and the punching needle is mounted in and used in the handpiece to allow a part of the slit or the entire slit to be exposed in front of the handpiece. The above-described punching needle enables an inside of the punching needle to be directly and visually checked through the slit formed in the punching needle and enables the extraction target hair to be inserted into the punching needle from a side of the punching needle through the slit formed in the punching needle.

According to one embodiment of the present disclosure, an inside wall of the front end portion of the punching needle is configured to be inclined such that an inner diameter of the front end portion is gradually reduced toward a rear side thereof.

According to one embodiment of the present disclosure, there is provided a handpiece used to separate a follicle of an extraction target hair from a skin tissue of a patient while a punching needle is rotated. The handpiece according to one embodiment of the present disclosure includes an outer housing, a power generator provided in the outer housing, a spindle assembly configured to transmit a rotational force generated by the power generator, and a punching needle coupled to the front of the spindle assembly and inserted into patient's skin while being rotated by the rotational force generated by the power generator. The punching needle may be provided with a slit formed at one side of a front end portion thereof and extending rearward in a longitudinal direction of the punching needle, the inside of the punching needle may be directly and visually checked through the slit formed in the punching needle, and the extraction target hair may be inserted into the punching needle from a side of the punching needle through the slit formed in the punching needle.

According to one embodiment of the present disclosure, the handpiece may be configured to, after a punching operation is completed, return the punching needle to a position before the punching operation.

According to one embodiment of the present disclosure, the handpiece may further comprise an encoder configured to detect a rotation state of the power generator, so that the handpiece may be configured to return the punching needle upon completion of the punching operation to a position before the punching operation on the basis of rotation state information detected by the encoder.

According to one embodiment of the present disclosure, the handpiece may further include a blade provided at a front end portion side thereof and configured to cut the extraction target hair, and the blade is configured to cut the hair, which is exposed to the outside through the slit of the punching needle, according to the rotation of the punching needle.

According to one embodiment of the present disclosure, a front cover may be coupled to the front of the handpiece, and an extension part extending in front of the front cover may be formed on a part of a front end portion of the front cover to allow the blade to be formed on the extension part.

According to one embodiment of the present disclosure, the extension part of the front cover may be formed so as not to cover the slit formed in the punching needle.

In addition to the above, the punching needle and the handpiece according to the present disclosure may further include other additional components within the scope not impairing the technical idea of the present disclosure.

Advantageous Effects

A punching needle according to one embodiment of the present disclosure is configured to have a slit extending rearward from a front end portion in a longitudinal direction of the punching needle to enable an extraction target hair to be inserted from a side through the slit, so that it is possible to easily and quickly insert the hair into the punching needle even when the hair has a long length. Therefore, a punching operation may be quickly and stably performed to extract the hair without cropping hairs in the hair extraction region.

Further, since an operator may perform a punching operation while directly and visually checking a hair located inside a punching needle through a slit formed in the punching needle, it is possible to perform the punching operation in a direction of the hair and in a state in which the extraction target hair is more easily centered in the punching needle, and as a result, the possibility of the punching needle cutting or damaging the hair follicle in a process of extracting a hair may be greatly reduced.

Further, a handpiece according to one embodiment of the present disclosure is configured to, after completing the punching operation, allow operation of the punching needle to be stopped in a state in which the punching needle upon completion of the punching operation is returned to a position before the operation, so that the slit formed in the punching needle may always be located at the same position after the punching operation is completed. Therefore, the punching needle may always be stopped and positioned in a state in which the slit is positioned within an operator's view, the operator may easily and conveniently insert/remove the hair into/from the punching needle through the slit and may effectively perform the hair extraction operation while directly and visually checking the inside of the punching needle through the slit.

Further, a handpiece according to an embodiment of the present disclosure is configured to have a blade provided at a front end portion side thereof to allow a hair to be cut by the relative rotation between a punching needle and the blade, so that even when the hair is extracted in a state in which a length of the hair is long, the extraction target hair is automatically cut to an appropriate length in a process of separating a follicle of the extraction target hair. Therefore, even when the hair is extracted in a state in which a length of the hair is long, it is possible to prevent the hair extraction from becoming difficult due to twisting or entanglement of the extraction target hair with surrounding hairs, and it is possible to quickly and effectively extract the hair.

DETAILED DESCRIPTION

Figure 1:
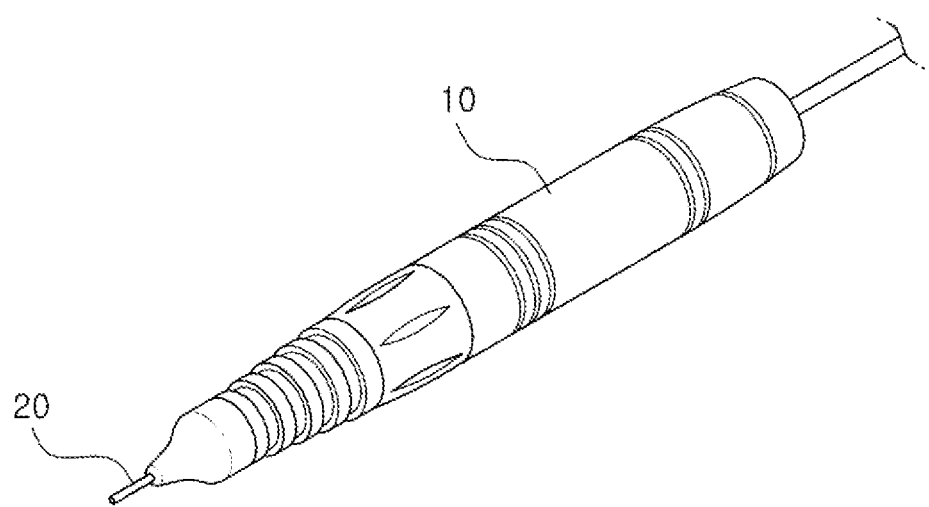
FIG. 1 illustrates an example of a conventional handpiece which may be employed in a follicular unit extraction.
Figure 2:
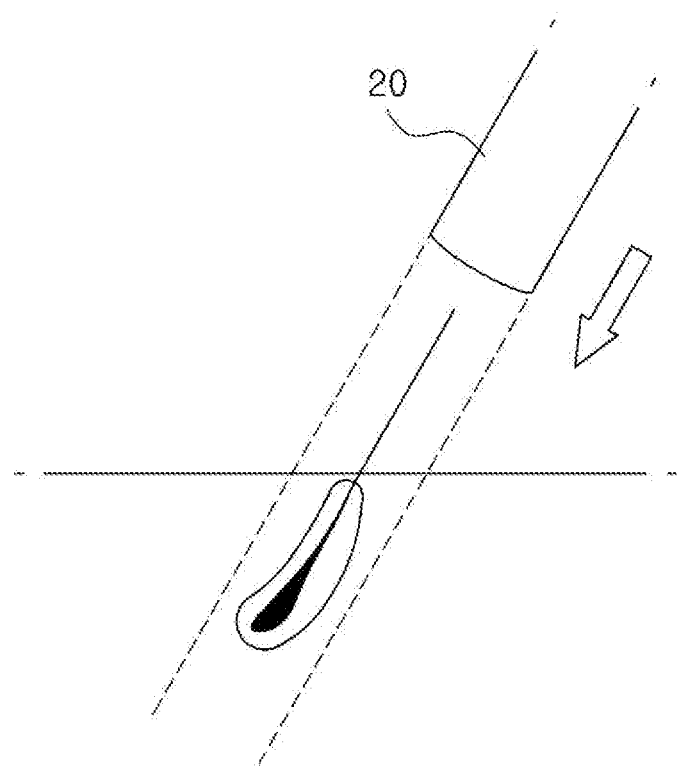
FIG. 2 illustrates an example of in which an extraction target hair is inserted into a punching needle of the handpiece.
Figure 3A:
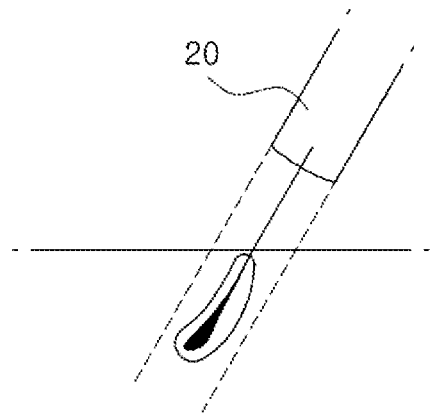
FIG. 3A illustrates an example of in which a hair follicle is separated by the punching needle.
Figure 3B:
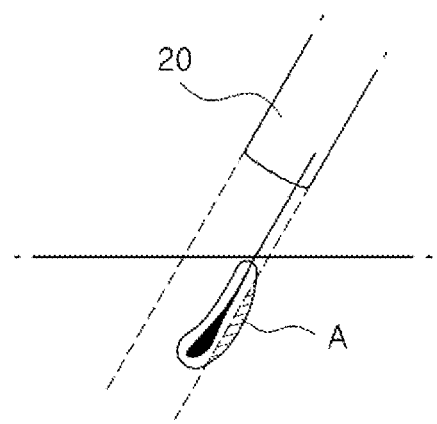
FIG. 3B illustrates an example of in which a hair follicle is separated by the punching needle.
Figure 3C:
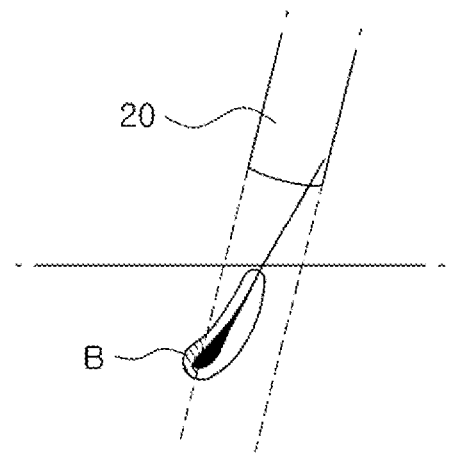
FIG. 3C illustrates an example of in which a hair follicle is separated by the punching needle.

Hereinafter, exemplarily embodiments of the present disclosure will be described in detail with reference to the accompanying drawings so that those skilled in the art to which the present disclosure pertains may easily carry out the present disclosure.

In order to clearly describe the present disclosure, a detailed description on parts which are not related to the present disclosure will be omitted, and the same components will be described by the same reference numerals throughout the specification. In addition, since a shape and size of each component shown in the drawings are arbitrarily shown for convenience of explanation, the present disclosure is not necessarily limited to the illustrated shape and size. That is, specific shapes, structures, and characteristics described in the specification may be modified and implemented from one embodiment to another embodiment without departing from the spirit and scope of the present disclosure, and it should be understood that a position or arrangement of individual component may be changed without departing from the spirit and scope of the present disclosure. Therefore, the following detailed description is not intended to be construed in a limiting sense, and the scope of the present disclosure should be construed as encompassing the scope of the appended claims and all equivalents thereof.

Exemplarily Embodiments of the Present Disclosure

Figure 4:
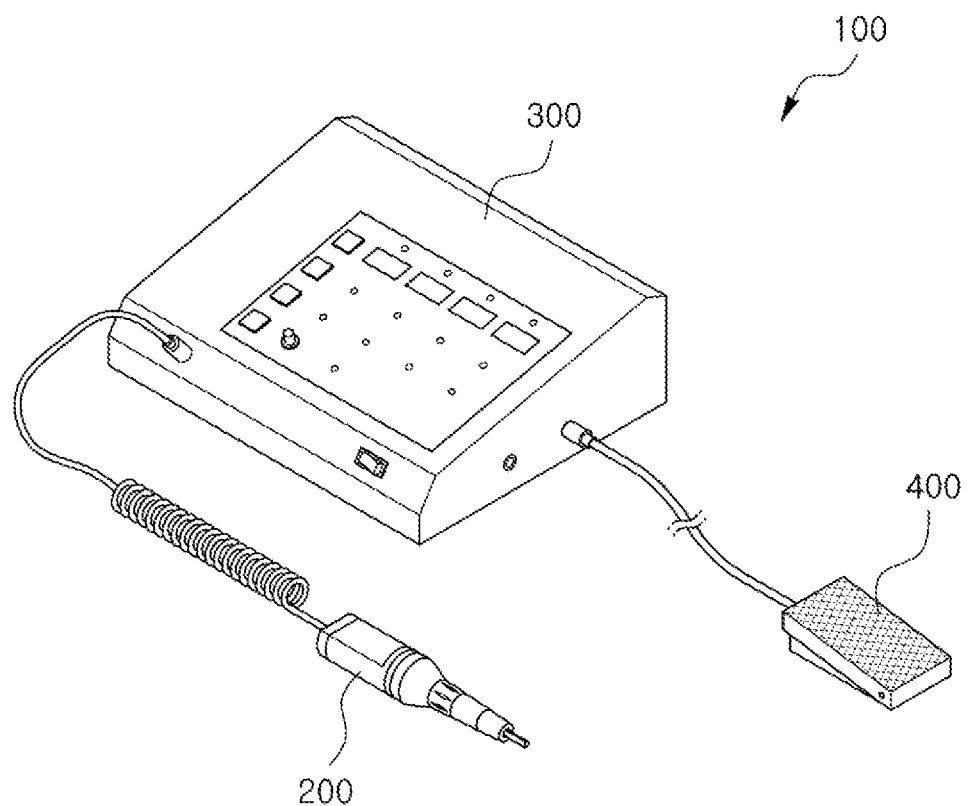
FIG. 4 illustrates an example of a configuration of a punching system according to one embodiment of the present disclosure.
Figure 5:
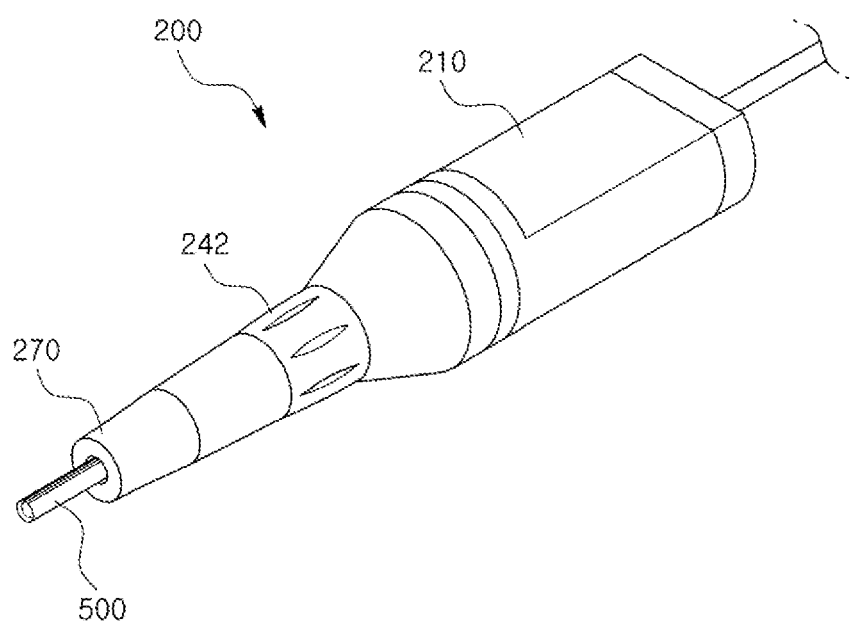
FIG. 5 illustrates an example of a configuration of a handpiece according to one embodiment of the present disclosure.
Figure 6:
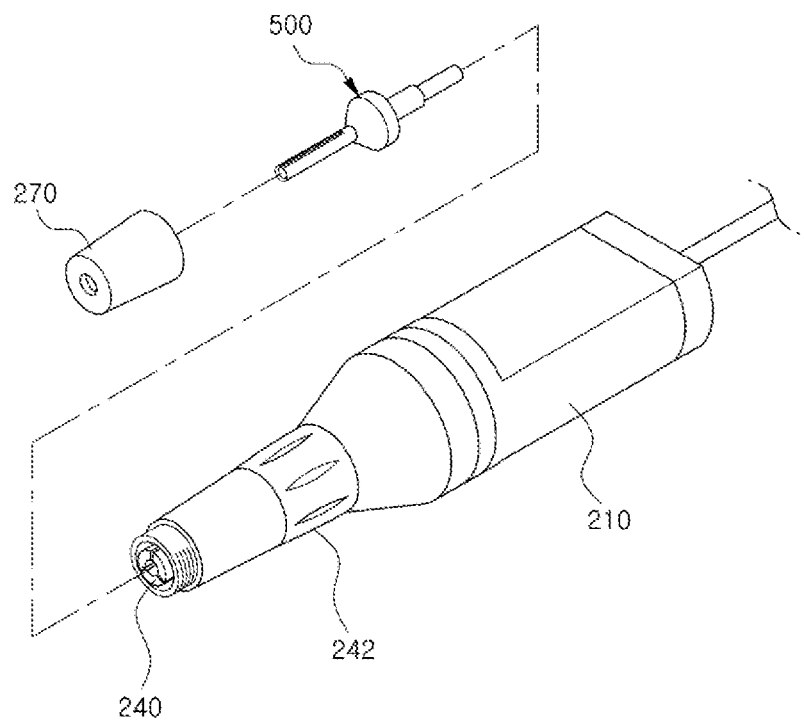
FIG. 6 illustrates an example of a configuration of a handpiece according to one embodiment of the present disclosure.

A punching system 100 according to one embodiment of the present disclosure is exemplarily illustrated in FIG. 4. As illustrated in FIG. 4, the punching system 100 may include a handpiece 200 configured to be grasped by an operator to perform a punching operation, a main body 300 configured to control operation of the handpiece 200, a manipulator 400 configured to turn on/off the operation of the handpiece 200. Although the manipulator 400 is implemented as a pedal in the embodiment shown in the drawing, the manipulator 400 may be provided in any form other than the pedal (e.g., an operation button provided on the handpiece 200 or the main body 300).

The handpiece 200 has a punching needle 500 mounted in the front thereof to perform a function of puncturing a patient's skin with the punching needle 500 and separating a hair follicle to be extracted from skin tissue surrounding the hair follicle. According to one embodiment of the present disclosure, the handpiece 200 may be provided with components such as a power generator (for example, an electric motor), a spindle assembly (a power transmitting part), etc., such as a conventional handpiece.

In FIGS. 5 to 9, the handpiece 200 according to one embodiment of the present disclosure is exemplarily illustrated. As illustrated in the drawings, the handpiece 200 according to one embodiment of the present disclosure may include an outer housing 210 forming a body, a power generator 220 provided in the outer housing 210 to generate power required for rotating the punching needle 500, a spindle assembly 230 (power transmitting part) configured to transmit the power generated by the power generator 220, and the like.

According to one embodiment of the present disclosure, a mounting part 240 for coupling the punching needle 500 is provided at the front of the spindle assembly 230. The mounting part 240 provided on the spindle assembly 230 may be implemented in a manner similar to a conventional handpiece. According to one embodiment of the present disclosure, the handpiece 200 may be configured so that a collet chuck (the mounting part 240) is provided at the front of the spindle assembly 230 connected to the power generator 220 to grasp the punching needle 500 through a chucking operation of the collet chuck. For example, the handpiece may be configured so that when a user rotates a collet chuck manipulating part 242 formed on the outer housing 210 of the handpiece 200 in one direction, a diameter of the collet chuck decreases and the collet chuck grasps the punching needle 500, and when the user rotates the collet chuck manipulating part 242 in a direction opposite the one direction, an inner diameter of the collet chuck is increased and a coupling between the punching needle 500 and the collet chuck is released. Since such a mounting part 240 may be formed to have a structure and shape which are similar to those of a mounting part of a conventional medical handpiece or an electric drill and the present disclosure is not characterized in a structure of the mounting part 240 for mounting the punching needle 500, a more detailed description thereof will be omitted herein.

The power generator 220 performs a function of generating a rotational force for rotating the punching needle 500 to enable the punching needle 500 to be easily inserted into the patient's skin. The power generator 220 may be implemented using an electric motor or the like as in a conventional medical handpiece, and may be configured to rotate the punching needle 500 in one direction or both directions using a rotational force generated by the power generator 220. However, when the punching needle 500 is inserted into the patient's skin while the punching needle 500 is continuously rotated in only one direction, a stress in the same direction may be continuously applied to the patient's skin to cause more damage to the patient's skin and an extracted hair may be twisted in a rotating direction to increase a risk of damage to the hair follicle. Therefore, it may be more advantageous that the power generator 220 is configured to rotate the punching needle 500 alternately in both directions.

Figure 7:
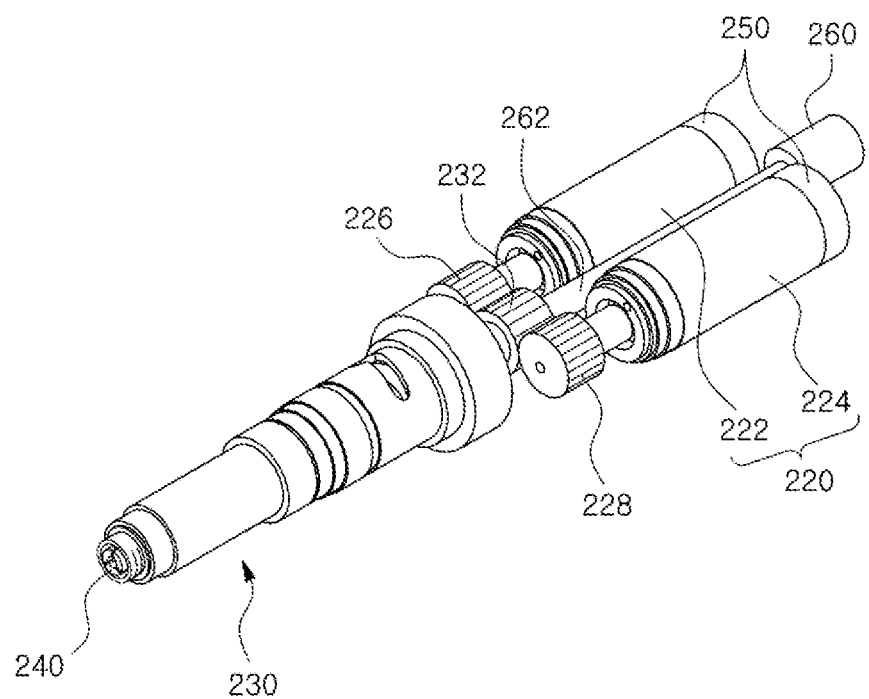
FIG. 7 illustrates an example of a configuration of a handpiece according to one embodiment of the present disclosure.

A structure of the handpiece 200 configured to enable the punching needle 500 to be rotated in both directions according to one embodiment of the present disclosure is exemplarily illustrated in FIG. 7. As illustrated in the drawing, the handpiece 200 according to one embodiment of the present disclosure may be configured to rotate the punching needle 500 in both directions by configuring the power generator 220 with two electric motors.

Specifically, the handpiece 200 according to one embodiment of the present disclosure may include a first motor 222 configured to rotate the spindle assembly 230 and the punching needle 500 mounted in the front of the spindle assembly 230 in one direction (for example, a clockwise direction) and may include a second motor 224 configured to rotate the spindle assembly 230 and the punching needle 500 in the other direction (for example, a counterclockwise direction). A first gear 226 and a second gear 228 are connected to output shafts of the first motor 222 and the second motor 224, respectively, to transmit rotational force generated by the motors to the spindle assembly 230. In particular, the first gear 226 connected to the output shaft of the first motor 222 and the second gear 228 connected to the output shaft of the second motor 224 are connected to an intermediate gear 232 provided on the spindle assembly 230, so that the spindle assembly 230 and the punching needle 500 may be rotated by the rotational force generated by the first motor 222 and the second motor 224.

According to one embodiment of the present disclosure, the first motor 222 and the second motor 224 may be configured to be alternately operated at regular time intervals by control of a controller (not shown). For example, when the first motor 222 is rotated according to a command of the controller, a rotational force generated by the first motor 222 is transmitted to the spindle assembly 230 through the first gear 226 and the intermediate gear 232, and the spindle assembly 230 and the punching needle 500 mounted in the front of the spindle assembly 230 are thus rotated in one direction. Thereafter, when rotation of the first motor 222 is stopped by the controller and the second motor 224 is controlled to be rotated after a predetermined amount of time has elapsed, a rotational force generated by the second motor 224 is transmitted to the spindle assembly 230 through the second gear 228 and the intermediate gear 232, and the spindle assembly 230 and the punching needle 500 mounted in the front of the spindle assembly 230 are rotated in the opposite direction. According to the above configuration, since the punching needle 500 is inserted into the patient's skin while rotating alternately in both directions, it is possible to stably insert the punching needle 500 into the patient's skin while less stress is applied to the of the patient's skin.

Figure 8:
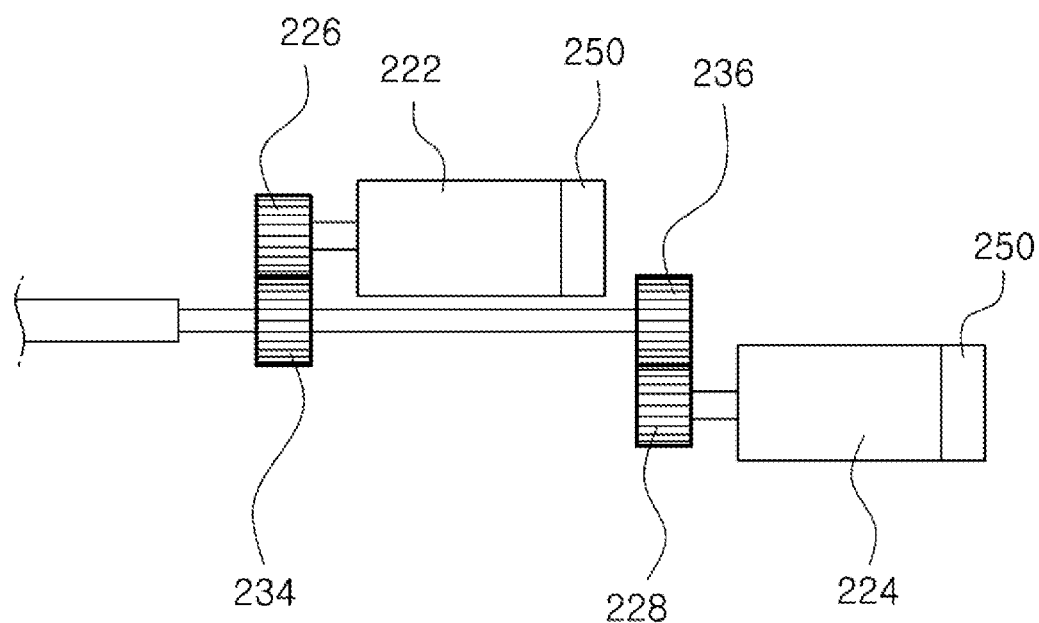
FIG. 8 illustrates an example of a configuration of a handpiece according to one embodiment of the present disclosure.
Figure 9:
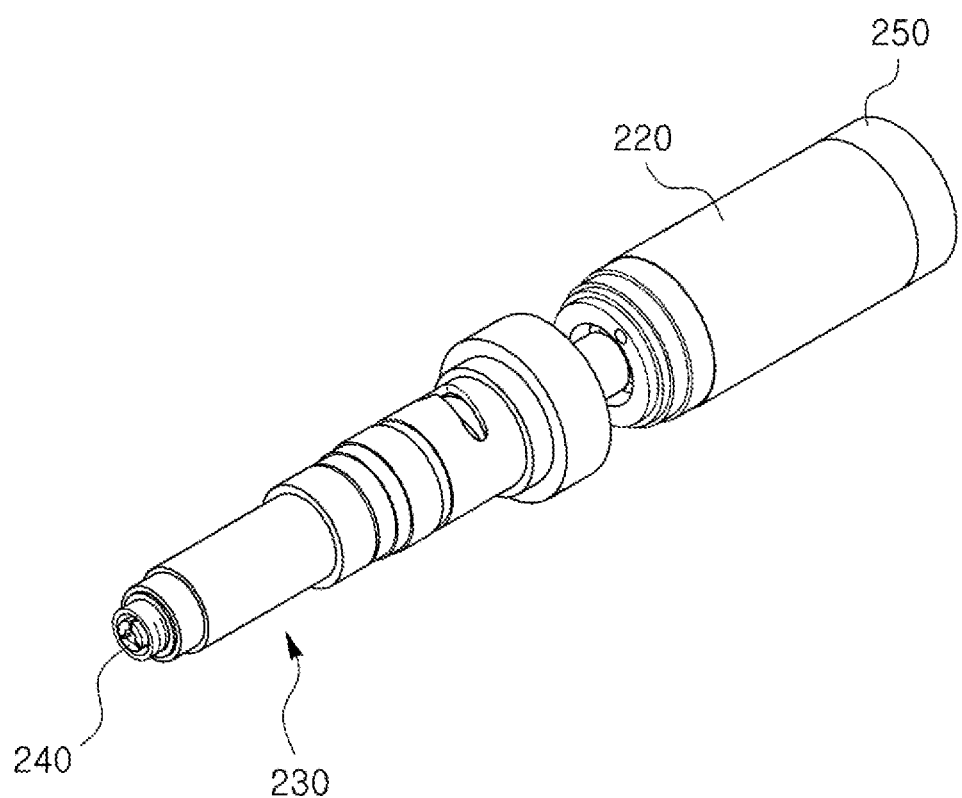
FIG. 9 illustrates an example of a configuration of a handpiece according to one embodiment of the present disclosure.

According to one embodiment of the present disclosure, the power generator 220 may be configured to have various structures and arrangements other than those shown in FIG. 7. For example, although FIG. 7 illustrates a configuration in which the output shafts of the first motor 222 and the second motor 224 are connected to the spindle assembly 230 through one intermediate gear 232, the first motor 222 and the second motor 224 may be connected to the spindle assembly 230 through separate intermediate gears (a first intermediate gear 234 and a second intermediate gear 236) provided on the spindle assembly 230, as shown in FIG. 8. Furthermore, the handpiece 200 according to one embodiment of the present disclosure may be configured to rotate the punching needle 500 in both directions with one electric motor, which may be rotated in both directions according to a control signal of the controller, as shown in FIG. 9, and may be configured to rotate the punching needle 500 in only one direction as in the conventional handpiece.

In the meantime, according to one embodiment of the present disclosure, the electric motor constituting the power generator 220 of the handpiece 200 may further include an encoder 250 for sensing a rotation state of the motor. For example, the encoder 250 may be configured to be mounted to the rear of the electric motor to perform a function of detecting the amount of rotation (rotation angle) of the electric motor and transmitting the detected amount of rotation to the controller (not shown). Rotation state information of the electric motor measured by the encoder 250 as described above may be used to control rotation of the punching needle 500 when a punching operation for extracting hair is performed or to, upon completion of the punching operation, control the punching needle 500 to be returned to an original position thereof before a punching operation. However, such an encoder 250 is not necessarily provided, and it is of course possible to form the power generator 220 of the handpiece 200 while omitting the encoder 250.

According to one embodiment of the present disclosure, the handpiece 200 may further include a light source 260 for assisting a user in setting a punching position. The light source 260 may display the punching position on the patient's skin to perform a function of assisting the user with stably setting the position of the punching needle 500.

As described above, in order to accurately perform a hair follicle separating operation using the handpiece, it is necessary to perform the punching operation in a state in which the punching needle is positioned so that a hair (preferably a hair follicle) to be extracted is positioned at a center of the punching needle. However, since the punching needle is usually formed of a metal material (for example, stainless steel) having high strength so as to stably penetrate the patient's skin, the user cannot visually check the inside of the punching needle, so that there is a great difficulty in setting the position of the punching needle. For this reason, in many cases, the punching operation is performed in a state in which the punching needle is eccentrically biased or deflected towards one side, such that the hair follicle is cut or damaged by the punching needle in a punching process. In contrast, since the handpiece 200 according to one embodiment of the present disclosure is configured to indicate the punching position on the patient's skin using the light source 260, the user may set the position of the punching needle 500 more easily.

Figure 10:
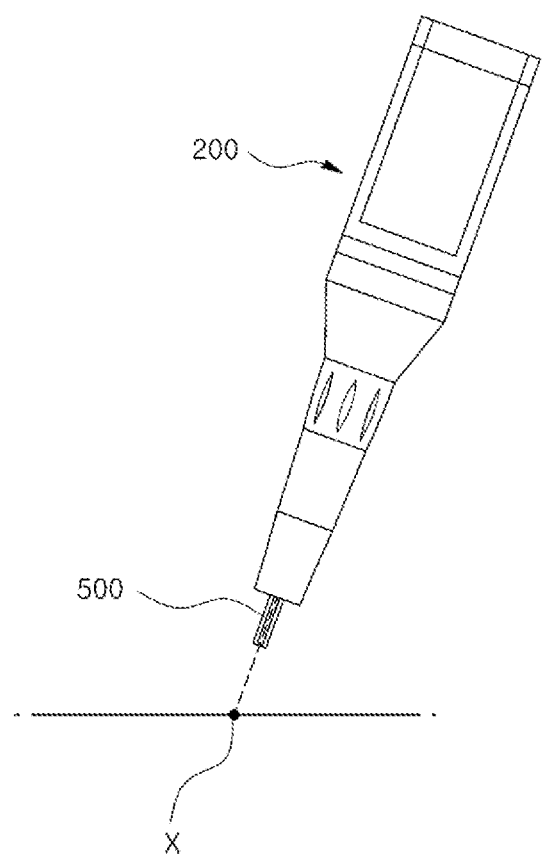
FIG. 10 illustrates an example of in which light guiding a punching position is emitted from the handpiece according to one embodiment of the present disclosure.

Specifically, according to one embodiment of the present disclosure, the handpiece 200 may be configured to be provided with the light source 260 which consists of a laser light source and is provided at a rear end thereof, and a light guide 262 which is provided at the front of the light source 260 for guiding the light generated by the light source 260. Due to the above configuration, laser light generated by the light source 260 may pass through the center portions of the light guide 262, the spindle assembly 230, and the punching needle 500, and be emitted in front of the handpiece 200 along a central axis of the handpiece 200 (see FIG. 10). Accordingly, the user may easily place the extraction target hair at a center of the punching needle 500 in (portion X in FIG. 10) by placing the extraction target hair at a region (portion X in FIG. 10) of the patient's skin to which the light is emitted, and it is possible to greatly reduce a risk of damaging the hair follicle during a process in which the hair is extracted.

In the embodiment illustrated in the drawings, the handpiece is configured to emit the laser light along a central axis of the punching needle 500 to display a center point of the punching needle on the patient's skin. However, the light which guides the punching position may be implemented to be emitted in various shapes (for example, circular band shape and the like) other than a point shape shown in the drawing and may be implemented by employing another known light source (for example, a light emitting diode (LED) or the like) other than the laser light. In addition, the light source 260 may be implemented to be mounted in another region of the handpiece 200 such as a front cover 270 or the spindle assembly 230, and it is of course possible to implement the handpiece while omitting the light source 260.

Meanwhile, a front cover 270 may be coupled to the front of the handpiece 200. The front cover 270 may be coupled to the front of the handpiece 200 to perform a function of adjusting a front exposed length of the punching needle 500.

Figure 11:
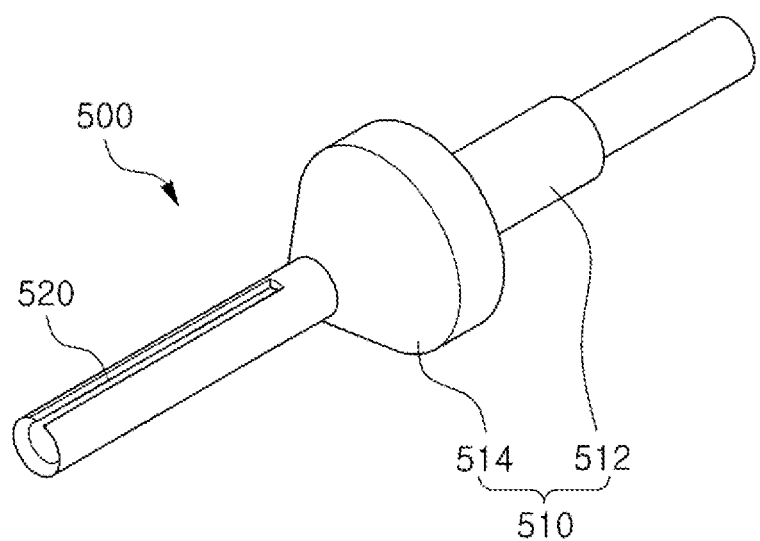
FIG. 11 illustrates an example of a punching needle according to one embodiment of the present disclosure.
Figure 12:
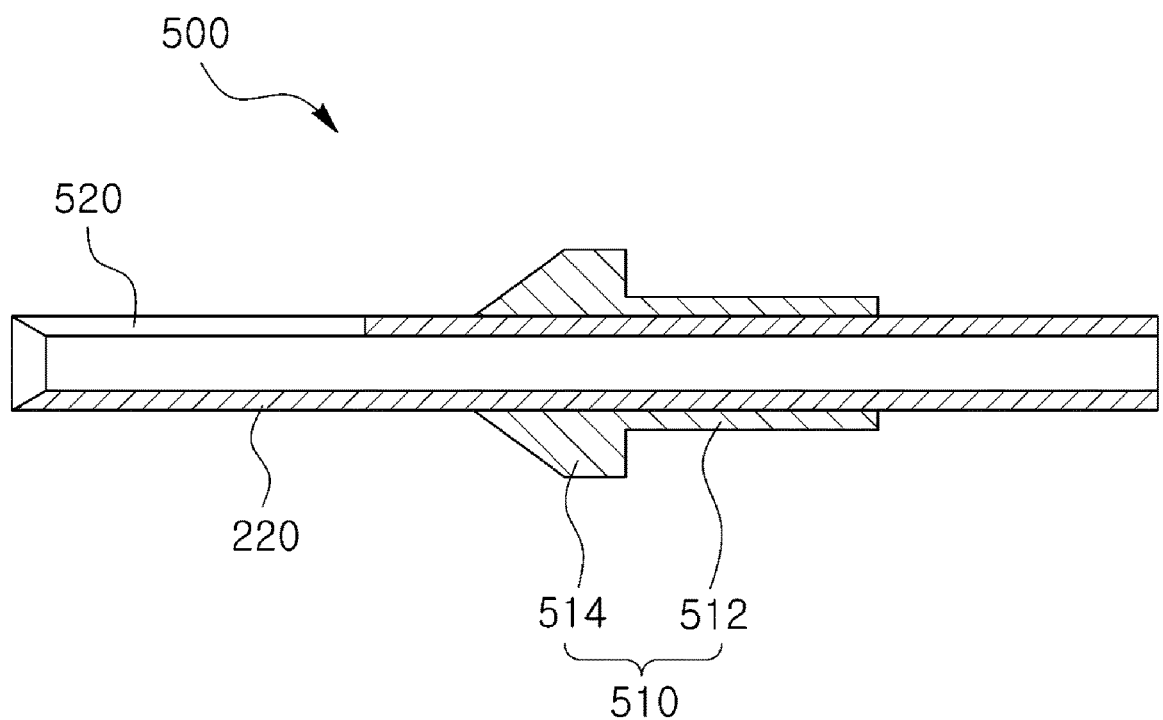
FIG. 12 illustrates an example of a punching needle according to one embodiment of the present disclosure.

Next, the punching needle 500 which is coupled to the front of the handpiece 200 and inserted into the patient's skin will be described in detail. Referring to FIGS. 11 and 12, a configuration of the punching needle 500 according to one embodiment of the present disclosure is exemplarily illustrated.

According to one embodiment of the present disclosure, the punching needle 500 may be formed in a shape which is generally similar to that of a conventional punching needle. For example, the punching needle 500 may be formed in the form of a hollow needle. In addition, a mounting hub 510 used to mount the punching needle 500 to the handpiece 200 may be provided on an outer circumference of the punching needle 500. Since the punching needle 500 is generally formed to have a very small diameter, when the punching needle 500 is mounted in the handpiece 200, a mounting operation may be troublesome, and there is a possibility of the punching needle 500 becoming deformed in a process in which the punching needle 500 is mounted to the handpiece 200. Like the punching needle 500 according to one embodiment of the present disclosure, on the contrary, when the mounting hub 510 having a larger diameter is formed on the outer circumference of the punching needle 500 and the punching needle 500 is then mounted in the handpiece 200 through the mounting hub 510, there may be an advantage in that the punching needle 500 may be more easily mounted in the handpiece 200. Such a mounting hub 510 may be formed integrally with the punching needle 500 or may be formed separately from the punching needle 500 and then coupled to the punching needle 500. However, the mounting hub 510 is not necessarily provided, and the punching needle 500 may be configured to be formed without the mounting hub 510 and to be directly mounted in the handpiece 200.

According to one embodiment of the present disclosure, the mounting hub 510 of the punching needle 500 may include a coupling portion 512 having a diameter greater than an outer diameter of the punching needle 500 and configured to surround a portion of the punching needle 500 and a flange portion 514 located in front of the coupling portion 512 and extending outward from the coupling portion 512 in a diameter direction. The coupling portion 512 is used to mount the punching needle 500 in the handpiece 200 and the flange portion 514 may be used as a stopper for preventing the punching needle 500 from being excessively inserted into the handpiece 200.

According to one embodiment of the present disclosure, an inside wall of a front end portion of the punching needle 500 may be formed to be inclined such that an inner diameter of the front end portion is gradually reduced toward a rear side thereof. When the front end portion is formed to have such a configuration, the patient's skin may be easily punctured by a sharpened end and the hair follicle may be guided by an inclined surface formed on the inside wall of the front end portion, so that it is possible to further reduce a risk of the punching needle 500 damaging the hair follicle.

Figure 13A:
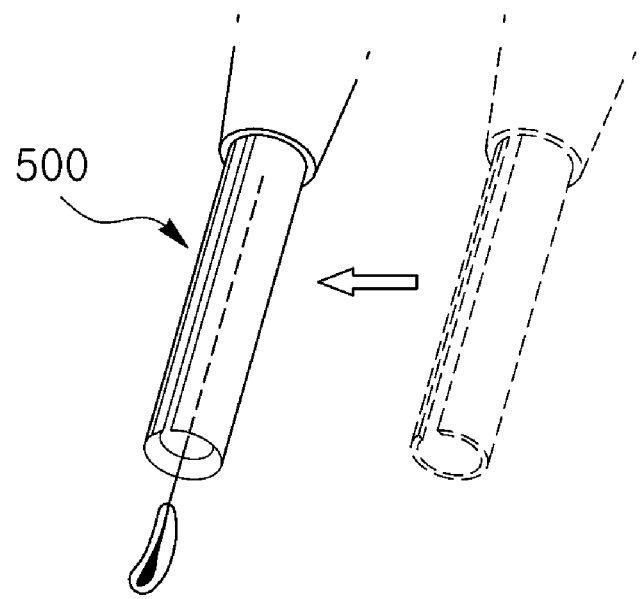
FIG. 13A illustrates an example of in which an extraction target hair is inserted into the punching needle of the handpiece according to one embodiment of the present disclosure.
Figure 13B:
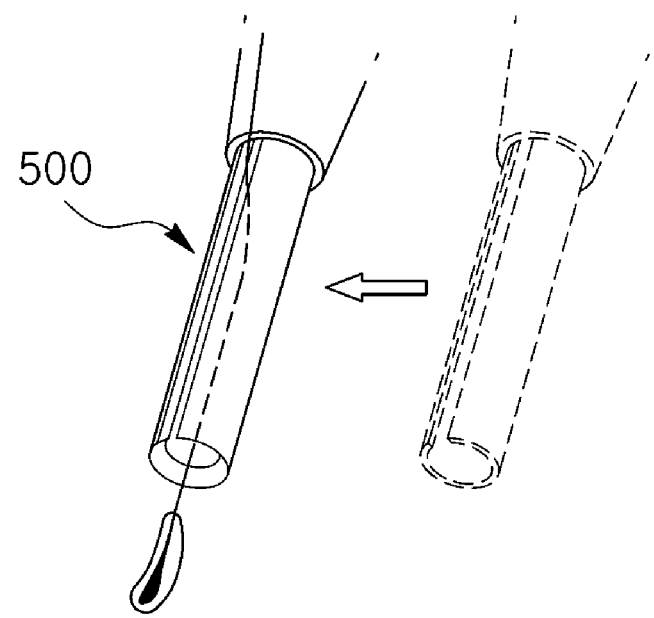
FIG. 13B illustrates an example of in which an extraction target hair is inserted into the punching needle of the handpiece according to one embodiment of the present disclosure.

According to one embodiment of the present disclosure, the punching needle 500 may have a slit 520 formed in one side of the front end portion and extending rearward in a longitudinal direction of the punching needle 500. When the slit 520 is formed in the front end portion of the punching needle 500 as described above, it is possible to insert the hair into the punching needle 500 from a side of the punching needle 500 as shown in FIG. 13A. Therefore, the hair may be easily inserted into the punching needle 500 without cropping the extraction target hair, and even when the hair is very long as shown in FIG. 13B, the punching operation becomes possible.

Furthermore, when the slit 520 is formed in the front end portion as in the punching needle 500 according to one embodiment of the present disclosure, the user may perform the punching operation while visually checking the extraction target hair, which is in the punching needle 500, through the slit 520. That is, the user may adjust a position and direction of the punching needle 500 while directly checking the inside of the punching needle 500 through the slit 520, and therefore, the user may insert the punching needle 500 into the patient's skin in a direction of the hair and in a state in which the extraction target hair is easily placed at a center of the punching needle 500, so that it is possible to greatly reduce a risk of the punching needle 500 cutting or damaging the hair follicle in a process of extracting a hair.

Meanwhile, in order for the above-described slit 520 of the punching needle 500 to be effectively operated, the handpiece 200 is preferably controlled such that the punching needle 500 is always positioned in the same direction before and after the punching operation. Since the electric motor is generally controlled to initiate rotation when an operation signal is supplied and to stop the rotation when the operation signal is blocked, if the handpiece according to one embodiment of the present disclosure (i.e., the handpiece 200 using the punching needle 500 provided with the slit 520) is formed using such a conventional electric motor, when the user takes his foot off the manipulator 400 (pedal) while the electric motor is driven by operation of the manipulator 400 (pedal), the operation signal supplied to the electric motor is blocked to stop the electric motor and the punching needle connected to the electric motor. As a result, the punching needle 500 is stopped while turned in an arbitrary direction according to the time at which the user takes his foot off the manipulator 400 (pedal), such that the slit 520 formed in the punching needle 500 may be positioned in a direction away from the user's view. However, when the slit 520 is turned in a different direction after the punching operation for inserting the punching needle 500 into the patient's skin is completed (for example, a position which is out of the user's view), it is inconvenient to remove the hair from the punching needle 500 after the punching operation and there may be an inconvenience in that the user has to reset the direction of the handpiece 200 to allow the slit 520 to come into the field of view for a subsequent punching operation. On the contrary, when rotation of the punching needle 500 is controlled so that the punching operation is completed in a state in which the punching needle 500 is returned to an original position thereof before the operation (that is, so that the rotation of the electric motor and the punching needle 500 is completed in a state in which the punching needle 500 is returned to the original position thereof before the operation), it is possible to eliminate the above-described inconvenience and perform the punching operation more effectively.

Such an automatic return function of the punching needle 500 may be implemented in the following manner. For example, the handpiece 200 according to one embodiment of the present disclosure may be implemented in a manner in which, when the operation of returning to the original position after the punching needle 500 has completed a periodic rotation pattern in which the punching needle is rotated alternately in both directions is regarded as a iteration of the punching operation, the operation of the handpiece is controlled to, when the operation signal from the manipulator 400 is blocked in the course of driving the handpiece 200, stop the rotation after further operation of the power generator causing the punching needle 500 to be rotated until the rotation pattern operation currently being performed is completed.

Figure 14A:
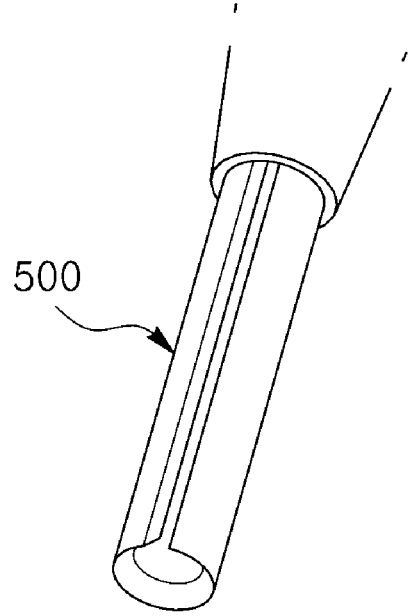
FIG. 14A illustrates an example of operating the handpiece according to one embodiment of the present disclosure (control of bidirectional rotation of the punching needle according to a rotational angle).
Figure 14B:
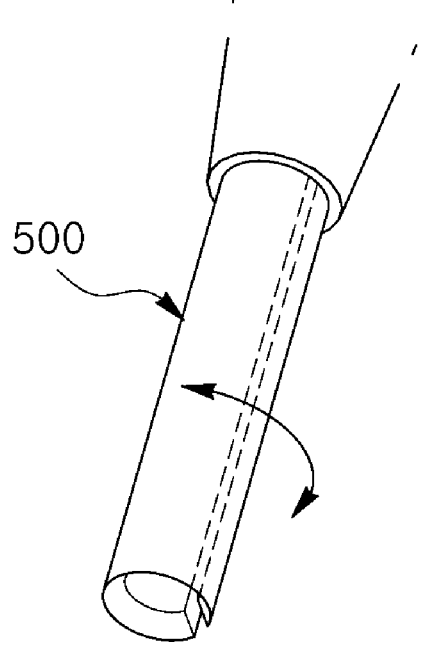
FIG. 14B illustrates an example of operating the handpiece according to one embodiment of the present disclosure (control of bidirectional rotation of the punching needle according to a rotational angle).

In FIGS. 14A and 14B, the punching operation performed in the handpiece 200 according to one embodiment of the present disclosure is exemplarily illustrated. For example, when the user operates the manipulator 400, the handpiece 200 according to one embodiment of the present disclosure alternately rotates the punching needle 500 in both directions using a driving force generated by the power generator, so that the user may stably insert the punching needle 500 into the patient's skin. Then, when the user stops the operation of the manipulator 400 to terminate the punching operation, the operation signal supplied to the power generator 220 is blocked to stop the operation of the power generator 220 and the rotation of the punching needle 500 connected to the power generator. Unlike with the conventional electric motor, here, the handpiece 200 may be controlled so that, without stopping the power generator 220 (electric motor) immediately after stopping the operation of the manipulator 400, the punching needle 500 is stopped after completing one iteration of the rotation pattern (for example, in the embodiment shown in FIGS. 14A and 14B, the operation in which, after the rotation from a standard position of FIG. 14A to a position of FIG. 14B, the punching needle is rotated in an opposite direction to return to the standard position of FIG. 14A) which is currently being performed by the punching needle 500.

Although the automatic return function of the punching needle 500 has been described with respect to the handpiece 200 configured to rotate the punching needle 500 in both directions in the above-described embodiment, the automatic return function of the punching needle 500 according to one embodiment of the present disclosure may be similarly implemented in the case of a handpiece 200 configured to rotate the punching needle 500 in only one direction. For example, in the case of a handpiece 200 in which the power generator 220 is configured using an electric motor rotated in only one direction, when the operation in which a rotational shaft of the electric motor is rotated by 360° is regarded as one iteration of the punching operation, the automatic return operation of the punching needle 500 may be implemented by, when operation of the manipulator 400 is stopped, controlling the power generator to be stopped after a 360° rotation pattern currently being performed is completed.

According to such an automatic return function of the punching needle 500, the punching needle 500 may always be positioned in the same state before and after the punching operation, and for this reason, the slit 520 formed in the punching needle 500 may be positioned in a certain direction (for example, in a direction in which the operator may check the slit 520), so that the operator may easily insert/remove the extraction target hair into/from the punching needle 500 through the slit 520 and may easily set the handpiece 200 while directly and visually checking the inside of the punching needle 500 through the slit 520.

Meanwhile, the handpiece 200 according to one embodiment of the present disclosure may be configured to rotate the punching needle 500 in both directions for more stable hair extraction as described above. However, in the case of hair transplantation procedure, it may be that the procedure should be performed while adjusting a rotational speed of the punching needle 500 according to the patient and procedure environment. In addition, even when the rotational speed of the punching needle 500 is set to a constant speed and the procedure is then performed, a frictional force applied to the punching needle 500 is varied depending on a condition of the patient's skin and an insertion depth of the punching needle 500, such that there may be a case in which the rotational speed of the punching needle 500 is unintentionally varied during the procedure. Therefore, in the case in which the electric motor is controlled to implement the bidirectional rotation so that a rotational direction of the electric motor is changed on the basis of a predetermined amount of time, as in a conventional bidirectional electric motor, it is difficult for the handpiece to cause the punching needle 500 to be rotated in both directions at an accurate angle desired by the operator and it may be difficult to accurately return the punching needle 500 to an original position thereof upon completion of the punching operation. Therefore, in order to perform a more accurate punching operation according to the operator's intention, it may be more preferable to control the handpiece so that the electric motor (and the punching needle 500) is rotated according to a predetermined angle.

Figure 15:
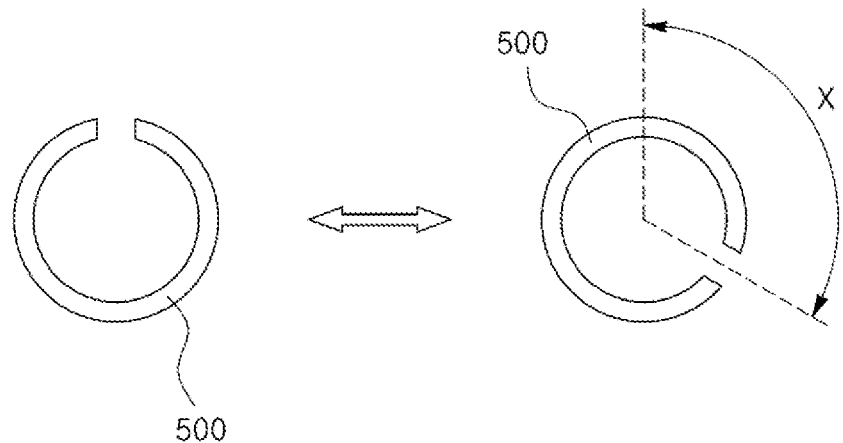
FIG. 15 illustrates an example of operating the handpiece according to one embodiment of the present disclosure (control of bidirectional rotation of the punching needle according to a rotational angle).

For example, the handpiece 200 according to one embodiment of the present disclosure may be controlled to change a rotation direction of the punching needle when the punching needle 500 is rotated by a predetermined punching angle X as shown in FIG. 15 (e.g., the punching needle is rotated in a clockwise direction from a state shown in FIG. 15A to a state shown in FIG. 15B and is then rotated in a counter-clockwise direction to the state shown in FIG. 15A again). According to such a configuration, the punching operation may be performed while the punching needle 500 is exactly rotated by the operator's desired angle, so that the punching operation may be performed more accurately, and the punching needle 500 may be accurately returned to its original position after the punching operation is completed, so that the handpiece according to one embodiment of the present disclosure (i.e., the handpiece 200 provided with the slit 520) may be used more effectively. On the other hand, for more effective hair extraction operation, it may be more preferable to configure the handpiece so that the operator may arbitrarily adjust and set the punching angle X based on the procedure conditions.

According to one embodiment of the present disclosure, the handpiece 200 is preferably configured so that the above-described punching angle X of the handpiece 200 may be set in a plurality of steps. In order to separate the extraction target hair from surrounding tissues for the hair extraction, the punching needle 500 of the handpiece 200 should be inserted into a subcutaneous layer located inside a dermis layer through the dermis layer located inside an epitheliopathy, starting from the epitheliopathy located on the outermost side of the patient's skin. However, while the epitheliopathy and the dermis layer located at the outside are formed of relatively hard tissue, the subcutaneous layer is composed of very soft tissue. Therefore, although it is necessary to rotate the punching needle 500 by a large angle in order to effectively cut through the tissue when the punching needle penetrates the epitheliopathy and/or the dermis layer, the punching needle 500 may be easily inserted into the patient's skin even when the punching needle 500 is rotated by a small angle when the punching needle 500 penetrates the subcutaneous layer. Rather, in the case of the subcutaneous layer composed of soft tissue, rotating the punching needle 500 by a very small angle in both directions to operate the punching needle such that it vibrates may help to stably insert the punching needle 500, while reducing a risk of damage to the surrounding tissue.

Figure 16A:
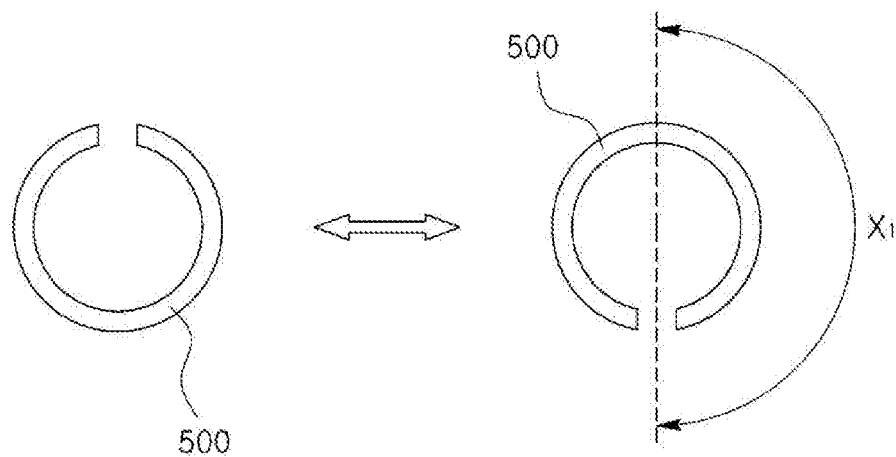
FIG. 16A illustrates an example of operating the handpiece according to one embodiment of the present disclosure (control of bidirectional rotation of the punching needle according to a rotational angle).
Figure 16B:
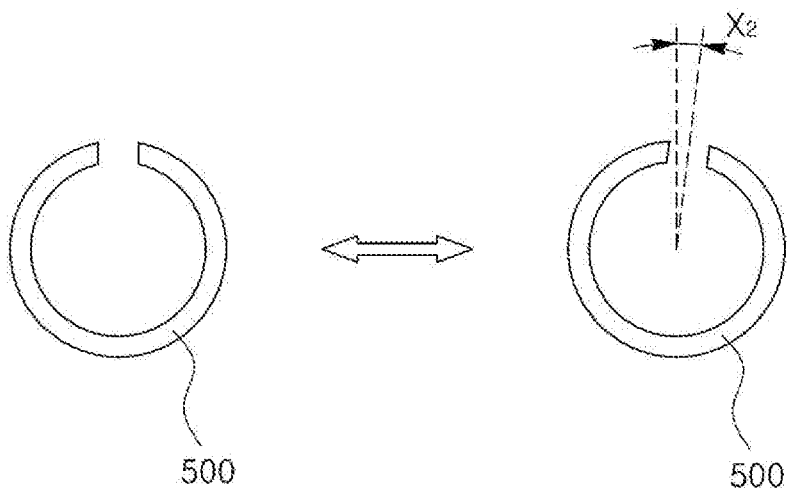
FIG. 16B illustrates an example of operating the handpiece according to one embodiment of the present disclosure (control of bidirectional rotation of the punching needle according to a rotational angle).

For this reason, the handpiece 200 according to one embodiment of the present disclosure may be configured to rotate the punching needle 500 by a large punching angle (a first punching angle $X_1$) at the beginning of the operation of penetrating the outer epithelial layer and the dermal layer, and then to rotate the punching needle 500 by a smaller punching angle (a second punching angle $X_2$). For example, the handpiece 200 according to one embodiment of the present disclosure may be configured to rotate the punching needle by the first punching angle $X_1$ (for example, 180°) a predetermined number of iterations (for example, three bidirectional rotations) (see FIG. 16A), and then to rotate the punching needle 500 by the second punching angle $X_2$ (for example, 5°) (see FIG. 16B). Alternatively, the handpiece may be configured to rotate the punching needle by the first punching angle $X_1$ (for example, 180°) for a predetermined initial time period (for example, 3 seconds) and then to rotate the punching needle 500 by the second punching angle $X_2$ (for example, 180°). According to this configuration, the punching needle 500 is rotated by a large angle and becomes inserted when the punching needle 500 is inserted into the relatively hard epithelial layer and/or the dermal layer, and the punching needle 500 may be rotated by a small angle to vibrate and become inserted when the punching needle 500 is inserted into the relatively soft subcutaneous layer, such that the punching needle 500 may be stably inserted into the patient's skin while minimizing damage to the patient's skin as much as possible. Here, it is more preferable that the time at which the punching angle is changed (for example, the number of iterations of the initial punching operation or the initial punching operation time) and the punching angles $X_1$ and $X_2$ at each step are configured to enable the user to arbitrarily adjust and set them according to procedure conditions. Although the case in which the punching operation is performed by setting the punching needle 500 in the two-steps of the punching angles $X_1$ and $X_2$ is exemplarily described in the above-described embodiment, the punching angle of the punching needle 500 may be set in three steps or more, and the rotational speed of the punching needle 500 may also be changed together with the punching angles $X_1$ and $X_2$.

Figure 17:
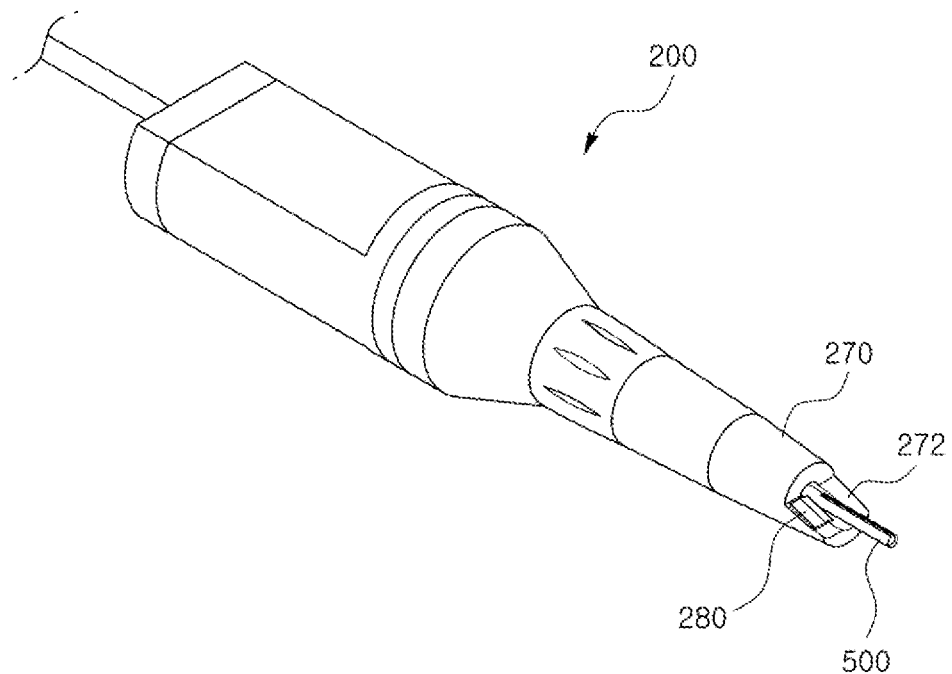
FIG. 17 illustrates an example of a configuration of a handpiece according to another embodiment of the present disclosure.
Figure 18:
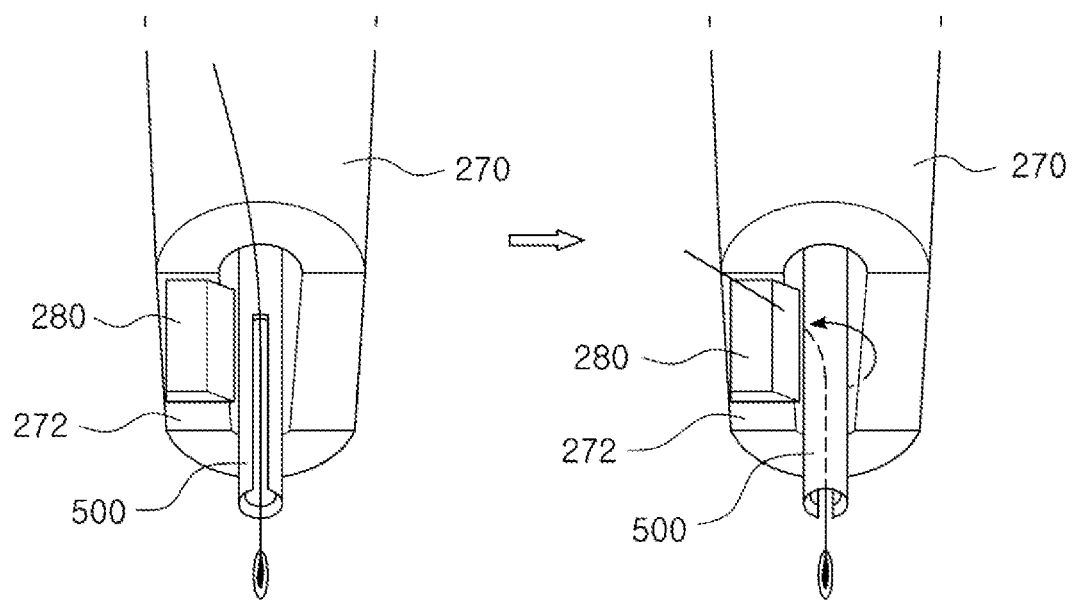
FIG. 18 illustrates an example of in which an extraction target hear is cut by a blade in the handpiece shown in FIG. 17.

Next, referring to FIGS. 17 and 18, another embodiment of the handpiece according to the present disclosure is exemplarily illustrated. The handpiece illustrated in FIGS. 17 and 18 differs from the above-described embodiment in only a structure of the front end portion side and the other structures may be configured in the same manner as the above-described embodiment, and accordingly, in this embodiment, only the structure of the front end side of the handpiece is described in detail, and a detailed description of other components will be omitted.

It is not preferable that the extraction target hair for the transplantation is extracted with an excessively short length, like the closely cropped hair as previously described above, and conversely, there may be a problem even when hair having an excessively long length is extracted. For example, an excessively long extraction target hair may easily be twisted or entangled with surrounding hairs in the process of extracting the hair, and therefore, it may be very troublesome to extract the separated hair to the outside. In order to solve the above problem, the handpiece 200 of the embodiment illustrated in FIGS. 17 and 18 is configured to separate the extraction target hair from the patient's skin using the punching needle 500 and at the same time to enable the extraction target hair to be cut to a length suitable for a hair transplantation.

Specifically, the handpiece 200 of the present embodiment is configured so that a blade 280 is provided at the front end portion to cut the hair, which is inserted in the punching needle 500, to an appropriate length using relative rotation between the punching needle 500 and the blade 280. For example, the handpiece 200 according to one embodiment of the present disclosure may be configured to provide a portion of the front end portion of the front cover 270 with an extension portion 272 extending forward and to form the blade 280 on such an extension portion 272. Here, it is preferable that the extension portion 272 is formed not to cover the slit 520 formed on the punching needle 500.

The operation principle of the handpiece 200 according to the present embodiment will be described in more detail. The punching needle 500 according to one embodiment of the present disclosure is provided with the slit 520 on one side of the front end portion, so that a long hair is inserted into the punching needle 500 at the state that a part of a long hair adjacent to the skin is positioned in the punching needle 500 and the end part of the hair is exposed to the outside through the slit 520 (see FIG. 13B and FIG. 18). In this state, when the punching needle 500 is rotated, the hair is rotated together with the punching needle 500 in a state in which the hair is wedged in the slit 520 of the punching needle 500.

When the hair passes, by rotation of the punching needle 500, over a position where the blade 280 is formed, the hair is caught between the punching needle 500 and the blade 280 and is cut (which is the same as the principle of cutting an object with a scissor; see FIG. 18). Therefore, the hair having a long length may be extracted while being cut into a length suitable for transplantation in the process of extracting a hair, so that it is possible to extract the hair even when the patient does not cut the hair at all. Therefore, repulsion and inconvenience may be further reduced in the patient, and it is possible for the patient to return to daily life more quickly.

While the present disclosure has been described with reference to the specific matters such as the specific components, the limited embodiments and the drawings, the above description is provided for better understanding of the present disclosure, this present disclosure is not limited to the above-described embodiment, and those skilled in the art to which the present disclosure pertains will make that various changes and modifications from the above disclosure. For example, although in the above-described embodiments, the configuration of the present disclosure is described using a handpiece including the electric motor provided therein, the punching needle according to the present disclosure (the punching needle provided with the slit) may also be mounted and used on a passive handpiece in which no electric motor is incorporated.

Accordingly, the spirit of the present disclosure should not be limited to the above-described embodiments, and the appended claims as well as the equivalents and the modifications thereof should be construed as being fall within the spirit and scope of the present disclosure.

What is claimed is:

1. A handpiece for separating a follicle of an extraction target hair from a skin tissue of a patient while a punching needle is rotated, the handpiece comprising;
   an outer housing;
   a power generator provided in the outer housing;
   a spindle assembly configured to transmit a rotational force generated by the power generator; and
   the punching needle coupled to a front of the spindle assembly and the punching needle is configured to be inserted into the patient's skin while being rotated by the rotational force generated by the power generator,
   wherein the punching needle is provided with a slit formed at one side of a front end portion thereof and extending rearward in a longitudinal direction of the punching needle, and
   wherein the handpiece is configured such that when a punching operation is completed, the punching needle is automatically returned to an original rotational position before the punching operation and then the rotation of the punching needle is stopped.

2. The handpiece of claim 1, further comprising an encoder configured to detect a rotation state of the power generator, and the handpiece is configured to automatically return the punching needle to the original rotational position on a basis of a rotation state information detected by the encoder.

3. The handpiece of claim 2, wherein the power generator is controlled to implement a bidirectional rotation.

4. The handpiece of claim 3, wherein the power generator is controlled to be rotated according to a predetermined punching angle.

5. The handpiece of claim 4, wherein the predetermined punching angle is set in a plurality of steps.

6. The handpiece of claim 5, wherein the predetermined punching angle comprises a first punching angle and a second punching angle,
   wherein the handpiece is configured to rotate the punching needle with the first punching angle for a predetermined number of iterations and then to rotate the punching needle with the second punching angle.

7. The handpiece of claim 5, wherein the predetermined punching angle comprises a first punching angle and a second punching angle,
   wherein the handpiece is configured to rotate the punching needle with the first punching angle for a predetermined operation time and then to rotate the punching needle with the second punching angle.

8. The handpiece of claim 1, further comprising a blade provided at a front end portion of the handpiece and configured to cut the extraction target hair.

9. The handpiece of claim 8, wherein:
   a front cover is coupled to the front end portion of the handpiece;
   an extension portion extending in front of the front cover; and
   the blade is formed on the extension portion.

10. The handpiece of claim 9, wherein the extension portion is formed so as not to cover the slit formed in the punching needle.

* * * * *